US009862652B2

(12) United States Patent
Dave et al.

(10) Patent No.: US 9,862,652 B2
(45) Date of Patent: Jan. 9, 2018

(54) MICROENCAPSULATED NITRIFICATION INHIBITOR COMPOSITION

(71) Applicant: DOW AGROSCIENCES LLC, Indianapolis, IN (US)

(72) Inventors: Hiteshkumar Dave, Carmel, IN (US); Lei Liu, Carmel, IN (US); Raymond E. Boucher, Jr., Lebanon, IN (US); Greg Powels, Carmel, IN (US); Alex Williams, Indianapolis, IN (US); Miriam Burkhart, Lafayette, IN (US)

(73) Assignee: Dow AgroSciences LLC, Indianapolis, IN (US)

(\*) Notice: Subject to any disclaimer, the term of this patent is extended or adjusted under 35 U.S.C. 154(b) by 162 days.

(21) Appl. No.: 14/702,126

(22) Filed: May 1, 2015

(65) Prior Publication Data
US 2015/0315091 A1    Nov. 5, 2015

Related U.S. Application Data

(60) Provisional application No. 61/988,056, filed on May 2, 2014.

(51) Int. Cl.
| | |
|---|---|
| *A61K 9/107* | (2006.01) |
| *C05C 9/00* | (2006.01) |
| *C05C 11/00* | (2006.01) |
| *C05G 3/08* | (2006.01) |
| *C05G 3/00* | (2006.01) |
| *C05C 1/00* | (2006.01) |
| *C05G 3/02* | (2006.01) |

(52) U.S. Cl.
CPC ................ *C05C 1/00* (2013.01); *A61K 9/107* (2013.01); *A61K 9/1075* (2013.01); *C05C 9/00* (2013.01); *C05C 11/00* (2013.01); *C05G 3/0017* (2013.01); *C05G 3/02* (2013.01); *C05G 3/08* (2013.01); *Y02P 60/218* (2015.11)

(58) Field of Classification Search
None
See application file for complete search history.

(56) References Cited

U.S. PATENT DOCUMENTS

| | | | |
|---|---|---|---|
| 3,135,594 A | 6/1964 | Goring | |
| 4,285,720 A | 8/1981 | Scher | |
| 4,475,939 A | 10/1984 | Michaud et al. | |
| 4,563,212 A * | 1/1986 | Becher | B01J 13/16 504/359 |
| 4,640,709 A * | 2/1987 | Beestman | A01N 25/28 264/4.7 |
| 4,746,513 A | 5/1988 | Smith | |
| 4,808,206 A | 2/1989 | Smith | |
| 4,936,901 A * | 6/1990 | Surgant, Sr. | A01N 25/28 504/133 |
| 4,985,064 A | 1/1991 | Redlich et al. | |
| 5,192,552 A | 3/1993 | Fekete et al. | |
| 5,925,464 A * | 7/1999 | Mulqueen | B01J 13/16 264/4.1 |
| 6,358,907 B1 | 3/2002 | Vitomir | |
| 8,377,849 B2 | 2/2013 | Wilson et al. | |
| 2005/0208089 A1 | 9/2005 | Asrar et al. | |
| 2005/0277549 A1 | 12/2005 | Seitz et al. | |
| 2006/0003014 A1 * | 1/2006 | Jadhav | A01N 25/28 424/490 |
| 2007/0027028 A1 * | 2/2007 | Pears | B01J 13/16 502/159 |
| 2008/0176745 A1 * | 7/2008 | Wilson | C05G 3/08 504/101 |
| 2009/0227458 A1 | 9/2009 | Boucher, Jr. et al. | |
| 2013/0157850 A1 * | 6/2013 | Wilson | C05G 3/08 504/101 |

FOREIGN PATENT DOCUMENTS

WO     03099005 A    12/2003

OTHER PUBLICATIONS

Yadav, S.K., et al., Microencapsulation in Polyurea Shell: Kinetics and Film Structure, AIChE Journal, Sep. 1996, pp. 2616-2626, vol. 42, No. 9.
Bertrand, F., International Search Report for PCT/US2008/000649, Jun. 23, 2008, pp. 1-3, EPO.
Ertrand, F., Written Opinion of the ISA for PCT/US2008/000649, 2008, pp. 1-5, EPO.
Ertrand, F., International Preliminary Report on Patentability for PCT/US2008/000649, Dec. 16, 2008, pp. 1-5, EPO.
Dow AgroSciences, LLC, State of the Art Report for Panama Patent Appl. No. 91398, Panama PTO, Jun. 16, 2017, pp. 1-2.
Hiteshkumar, D., International Search Report for PCT/US2015/028843, ISA/US, Jul. 21, 2015, pp. 1-3.
Hiteshkumar, D., Written Opinion for PCT/US2015/028843, ISA/US, Jul. 21, 2015, pp. 1-6.
Hiteshkumar, D., International Preliminary Report on Patentability for PCT/US2015/028843, IB, Nov. 8, 2016, pp. 1-7.

\* cited by examiner

*Primary Examiner* — Wayne Langel
(74) *Attorney, Agent, or Firm* — Charles W. Arnett; Faegre Baker Daniels LLP

(57) ABSTRACT

The present invention relates to an improved nitrification inhibitor composition and its use in agricultural applications.

20 Claims, No Drawings

US 9,862,652 B2

MICROENCAPSULATED NITRIFICATION INHIBITOR COMPOSITION

PRIORITY CLAIM

This application claims the benefit of U.S. Provisional Patent Application 61/988,056, which was filed on May 2, 2014, the disclosure of this provisional application, is incorporated herein by reference in its entirety.

FIELD OF THE INVENTION

The present invention relates to an improved nitrification inhibitor composition and its use in agricultural applications.

BACKGROUND AND SUMMARY (Trichloromethyl)pyridine compounds, such as nitrapyrin, have been used as nitrification inhibitors in combination with fertilizers as described in U.S. Pat. No. 3,135,594, which is herein incorporated by reference. These compounds maintain applied ammonium nitrogen in the ammonium form (stabilized nitrogen), which enhances crop performance. It would be desirable to broadly apply these compounds with nitrogenous fertilizer at sowing time, but due to potential volatility losses, these application methods are generally unsatisfactory. In addition nitrapyrin has been added to anhydrous ammonia, which by default must be injected into the soil.

Other nitrapyrin formulations have been applied to the surface of the soil, but must either be incorporated mechanically, or watered into the soil within 8 hours after application to overcome volatility losses. Finally, rapid or dump release capsule formulations of nitrapyrin encapsulated with lignin sulfonates have also been disclosed in U.S. Pat. No. 4,746,513, which is incorporated herein by reference. However, although the release of nitrapyrin is delayed by the encapsulation, the capsules release all of the nitrapyrin upon contact with moisture, exhibiting the same stability and volatility disadvantages of the prior application methods. Additionally, these formulations are difficult and costly to produce and cannot be used with liquid urea ammonium nitrate ("UAN") fertilizers.

Polycondensation encapsulation, as disclosed in U.S. Pat. No. 5,925,464, has been used to encapsulate agriculturally active ingredients, particularly to enhance handling safety and storage stability of the active ingredient by using polyurethane rather than polyurea encapsulants.

However, there remains a need to deliver nitrification inhibitors such as (trichloromethyl)pyridines, that exhibit greater long term stability in the field environment, while maintaining levels of efficacy comparable to that of un-encapsulated nitrification inhibitor formulations.

A first set of embodiments including a microcapsule suspension formulation, comprising: (a) a suspended phase, the suspended phase including a plurality of microcapsules, the microcapsules having a volume median particle size of from about 1 to about 10 microns, wherein the microcapsules comprise: (1) a microcapsule wall produced by an interfacial polycondensation reaction between a polymeric isocyanate and a polyamine to form a polyurea shell having a weight percentage of about 0.2 to about 40 percent of a total weight of the microcapsule suspension formulation, and (2) a substantially liquid core, the substantially liquid core is encapsulated within the polyurea shell, wherein the substantially liquid core includes no more than about 60 weight percent of a nitrification inhibitor, some of these embodiments, the nitrification inhibitor is 2-chloro-6-(trichloromethyl)pyridine, and the substantially liquid core in these embodiments includes no more than 1.0 weight percent of solid 2-chloro-6-(trichloromethyl)pyridine, as determined at a temperature greater than or equal to 15° C.; and (b) an aqueous phase, wherein the aqueous phase includes at least about 1.0 weight percent aromatic solvent, in some preferred embodiments the aromatic solvent in the aqueous phase is added after formation of the microcapsules.

A second set of embodiments including a microcapsule suspension formulation according to the first set of embodiments and, further including: at least one ionic stabilizer present in the aqueous phase.

A third set of embodiments including a microcapsule suspension formulation according to the first or second set of embodiments, wherein the aromatic solvent present in the aqueous phase is at least one compound selected from the group consisting of: light aromatics, naphthalene depleted light aromatics, heavy aromatics, and naphthalene depleted heavy aromatics.

A fourth set of embodiments including a microcapsule suspension formulation according to the third set of embodiments, wherein the aromatic solvent present in the aqueous phase is naphthalene depleted heavy C10-13 aromatics.

A fifth set of embodiments including a microcapsule suspension formulation according to the fourth set of embodiments wherein the aromatic solvent present in the aqueous phase comprises between about 1% by weight and about 10% by weight naphthalene depleted heavy C10-13 aromatics.

A sixth set of embodiments including a microcapsule suspension formulation according to the fourth set of embodiments wherein the aromatic solvent present in the aqueous phase, comprises between about 2% by weight and about 5% by weight naphthalene depleted heavy C10-13 aromatics.

A seventh set of embodiment including a microcapsule formulation according to the fourth set of embodiments, wherein the aromatic solvent present in the aqueous phase comprises between about 2.5% by weight and about 3.0% by weight naphthalene depleted heavy C10-13 aromatics.

An eighth set of embodiments including a microcapsule suspension formulation according to the third set of embodiments wherein the aromatic solvent present in the aqueous phase is heavy C10-13 aromatics.

A ninth set of embodiments including a microcapsule suspension formulation according to the eighth set of embodiments wherein the aromatic solvent present in the aqueous phase comprises between about 1% by weight and about 10% by weight heavy C10-13 aromatics.

A tenth set of embodiments including a microcapsule suspension formulation according to the eighth set of embodiments, wherein the aromatic solvent present in the aqueous phase comprises between about 2% by weight and about 5% by weight heavy C10-13 aromatics.

An eleventh set of embodiments including a microcapsule suspension formulation according to the eighth set of embodiments, wherein the aromatic solvent present in the aqueous phase comprises between about 2.5% by weight and about 3.0% by weight heavy C10-13 aromatics.

A twelfth set of embodiments including a microcapsule suspension formulation according to the first, second, third, fourth, fifth, sixth, seventh, eighth, ninth, tenths, or eleventh sets of embodiments wherein the microcapsules have a volume median particle size of from about 1 to about 5 microns.

A thirteenth set of embodiments including a microcapsule suspension formulation according to the first, second, third, fourth, fifth, sixth, seventh, eighth, ninth, tenths, eleventh, or twelfth sets of embodiments, wherein the ratio of the suspended phase a) to the aqueous phase b) is from about 1:0.75 to about 1:100.

A fourteenth set of embodiments including a microcapsule suspension formulation according to the thirteenth set of embodiments wherein the ratio of the suspended phase a) to the aqueous phase b) is from about 1:1 to about 1:7.

A fifteenth set of embodiments including a microcapsule suspension formulation according to the thirteenth set of embodiments wherein the ratio of the suspended phase a) to the aqueous phase b) is from about 1:1 to about 1:4.

A sixteenth set of embodiments including a microcapsule suspension formulation according to the first, second, third, fourth, fifth, sixth, seventh, eighth, ninth, tenths, eleventh, twelfth, thirteenth, fourteenth, or fifteenths sets of embodiments wherein the polymeric isocyanate is polymethylene polyphenylisocyanate.

A seventeenth set of embodiments including a microcapsule suspension formulation according to the first, second, third, fourth, fifth, sixth, seventh, eighth, ninth, tenths, eleventh, twelfth, thirteenth, fourteenth, fifteenths, or sixteenth embodiments further including a nitrogen fertilizer.

An eighteenth set of embodiments according the seventeenth embodiment wherein the nitrogen fertilizer is urea ammonium nitrate.

A nineteenth set of embodiments comprising the methods of suppressing the nitrification of ammonium nitrogen in a plant growth medium comprising the step of applying the microcapsule suspension formulations of the first, second, third, fourth, fifth, sixth, seventh, eighth, ninth, tenths, eleventh, twelfth, thirteenth, fourteenth, fifteenths, sixteenth, seventeenth, eighteenth, and nineteenth embodiments to a plant growth medium.

A twentieth set of embodiments according to the nineteenth set of embodiments wherein the formulations are incorporated into the growth medium.

A twenty first set of embodiments according to the twentieth set of embodiments wherein the formulations are applied to a plant growth medium surface.

A twenty second set of embodiments a method for inhibiting nitrification, wherein the formulation according to the first, second, third, fourth, fifth, sixth, seventh, eighth, ninth, tenths, eleventh, twelfth, thirteenth, fourteenth, fifteenths, or sixteenth is applied in combination with a pesticide or sequentially with a pesticide.

A twenty third set of embodiments including the method according wherein the twenty second set of embodiments wherein the formulations are applied along with a nitrogen fertilizer.

A twenty forth set of embodiments according the twenty third set of embodiments, wherein the nitrogen fertilizer is urea ammonium nitrate. A microcapsule suspension formulation, comprising: a suspended phase, the suspended phase including a plurality of microcapsules, the microcapsules having a volume median particle size of from about 1 to about 10 microns, wherein the microcapsules comprise: (1) a microcapsule wall produced by an interfacial polycondensation reaction between a polymeric isocyanate and a polyamine to form a polyurea shell having a weight percentage of about 0.2 to about 40 percent of a total weight of the microcapsule suspension formulation, and (2) a substantially liquid core, the substantially liquid core is encapsulated within the polyurea shell, wherein the substantially liquid core includes no more than 40 weight percent 2-chloro-6-(trichloromethyl)pyridine of the entire microcapsule; and (b) an aqueous phase, wherein the aqueous phase includes at least about 1.0 weight percent aromatic solvent, wherein the at least 1.0 percent aromatic solvent is added to the aqueous phase after the formation of the microcapsules.

Further disclosed herein is a microcapsule suspension formulation comprising: a suspended phase of a plurality of microcapsules having a volume median particle size of from about 1 to about 10 microns, wherein a microcapsule comprises: a microcapsule wall produced by an interfacial polycondensation reaction between a polymeric isocyanate and a polyamine to form a polyurea shell having a weight percentage of about 0.2 to about 15 percent of a total weight of the microcapsule suspension formulation, and a compound encapsulated within the polyurea shell wherein said compound is 2-chloro-6-(trichloromethyl)pyridine; and an aqueous phase including an ionic stabilizer and dispersed aromatic solvent.

In some embodiments, the dispersed aromatic solvent is at least one compound selected from the group consisting of: light aromatics, naphthalene depleted light aromatics, heavy aromatics, and naphthalene depleted heavy aromatics. In other embodiments, the dispersed aromatic solvent is naphthalene depleted heavy C10-13 aromatics. Still in other embodiments, the formulation comprises between about 1% by weight and about 10% by weight naphthalene depleted heavy C10-13 aromatics. In yet other embodiments, the formulation comprises between about 2% by weight and about 5% by weight naphthalene depleted heavy C10-13 aromatics.

In some embodiments, the formulation comprises between about 2.5% by weight and about 3.0% by weight naphthalene depleted heavy C10-13 aromatics. In still other embodiments, the dispersed aromatic solvent is heavy C10-13 aromatics. Still in other embodiments, the formulation comprises between about 1% by weight and about 10% by weight heavy C10-13 aromatics.

Further, in exemplary embodiments, the formulation comprises between about 2% by weight and about 5% by weight heavy C10-13 aromatics. Alternatively, the formulation comprises between about 2.5% by weight and about 3.0% by weight heavy C10-13 aromatics.

In further embodiments, the microcapsules have a volume median particle size of from about 1 to about 5 microns. In other embodiments, the ratio of the suspended phase a) to the aqueous phase b) is from about 1:0.75 to about 1:100. Still in other embodiments, the suspended phase a) to the aqueous phase b) is from about 1:1 to about 1:7. In further embodiments, the ratio of the suspended phase a) to the aqueous phase b) is from about 1:1 to about 1:4.

Also disclosed is a microcapsule suspension wherein the polymeric isocyanate is polymethylene polyphenylisocyanate. In some embodiments, the polyamine is selected from ethylenediamine and diethylenetriamine.

Still further disclosed is a fertilizer composition comprising: a nitrogen fertilizer and the microcapsule suspension formulation described above. In other embodiments, the nitrogen fertilizer is urea ammonium nitrate.

Also disclosed herein is a method of suppressing the nitrification of ammonium nitrogen in growth medium comprising applying the microcapsule suspension formulation described above to said growth medium. In further embodiments, the formulation is incorporated into the growth medium. In still further embodiments, the formulation is applied to a growth medium surface. In other embodiments, the formulation is applied in combination with a pesticide or sequentially with a pesticide.

In still further embodiments, the formulation is applied with a nitrogen fertilizer. The nitrogen fertilizer can be urea ammonium nitrate.

The microcapsule suspension formulation of the present invention is stable and allows for delayed incorporation of nitrogen in crops, thus providing agronomic and environmental benefits. Surprisingly it has been discovered that a composition of microencapsulated (trichloromethyl)pyridine compounds, such as nitrapyrin, has superior performance when compared to unencapsulated compositions of nitrapyrin, even when incorporated into the soil.

DETAILED DESCRIPTION (Trichloromethyl)pyridine compounds useful in the composition of the present invention include compounds having a pyridine ring which is substituted with at least one trichloromethyl group and mineral acid salts thereof. Suitable compounds include those containing chlorine or methyl substituents on the pyridine ring in addition to a trichloromethyl group, and are inclusive of chlorination products of methyl pyridines such as lutidine, collidine and picoline. Suitable salts include hydrochlorides, nitrates, sulfates and phosphates. The (trichloromethyl)pyridine compounds useful in the practice of the present invention are typically oily liquids or crystalline solids dissolved in a solvent. Other suitable compounds are described in U.S. Pat. No. 3,135,594. A preferred (trichloromethyl)pyridine is 2-chloro-6-(trichloromethyl)pyridine, also known as nitrapyrin, and the active ingredient of the product N-SERVE™. (Trademark of Dow AgroSciences LLC).

The utility of compounds such as nitrapyrin has been greatly increased by encapsulating such compounds along with suitable solvents in microcapsules. Especially useful microcapsules are comprised of a nitrapyrin/hydrophobic solvent substantially liquid core surround by a polyurea shell. The selection of microcapsules of appropriate volume and shell thickness, and composition can be suspended in, stored in, and applied in an aqueous phase. Such useful formulations are disclosed in U.S. patent application Ser. No. 12/393,661 filed on Feb. 26, 2009, publication number U.S. 2009-0227458 A1 published on Sep. 10, 2009; U.S. patent application Ser. No. 12/009,432, filed Jan. 18, 2008, publication number U.S. 2008-0176745 A1 published on Jul. 24, 2008 and now issued as U.S. Pat. No. 8,377,849 issued on Feb. 19, 2013; and U.S. Provisional Application Ser. No. 60/881,680 filed on Jan. 22, 2007, which are all expressly incorporated by reference herein in their entirety as if each were incorporated by reference individually.

While the microcapsule aqueous suspensions referred to above are more stable than un-encapsulated nitrapyrin in an aqueous solution under certain conditions, it has been observed that crystals of nitrapyrin can form in the aqueous phase of a microcapsule suspension of nitrapyrin during storage. Formation of crystalline nitrapyrin in an aqueous microcapsule suspension of nitrapyrin appears to be favored over a very narrow temperature range of about −50 C to about 150 C during long period of storage, more particularly about 00 C to 100 C (degrees centigrade). The weight percentage of crystalline nitrapyrin in the bulk aqueous phase of the microcapsule suspension accumulates over time. Depending upon how the microcapsule suspensions are handled, the presence of measurable levels of crystalline nitrapyrin in the aqueous phase can be of little or no consequence or problematic. The presence of even about 0.1 wt. percent crystalline nitrapyrin or above in the aqueous phase of the microcapsule suspension can be especially problematic if the suspension is applied by spraying the suspension through a fine point nozzle with a sprayer containing inline screens.

In order to inhibit or at least appreciably slow the formation on nitrapyrin crystal in the aqueous phase, disclosed herein is a microcapsule suspension formulation composition that includes at least 1 wt. percent aromatic solvent present in the aqueous phase of the microcapsule suspension. In some embodiments, the solvent is added to the aqueous phase of the microcapsule suspension before the accumulation of a problematic level of crystalline nitrapyrin in the aqueous phase. In some embodiments, the solvent is added to the aqueous phase of the suspension after problematic levels of crystalline nitrapyrin accumulates in the aqueous phase of the suspension.

Examples of typical solvents which can be used to dissolve crystalline (trichloromethyl)pyridine compounds in the organic phase of the microcapsules include aromatic solvents, particularly alkyl substituted benzenes such as xylene or propylbenzene fractions, and mixed naphthalene and alkyl naphthalene fractions; mineral oils; kerosene; dialkyl amides of fatty acids, particularly the dimethylamides of fatty acids such as the dimethyl amide of caprylic acid; chlorinated aliphatic and aromatic hydrocarbons such as 1,1,1-trichloroethane and chlorobenzene; esters of glycol derivatives, such as the acetate of the n-butyl, ethyl, or methyl ether of diethyleneglycol and the acetate of the methyl ether of dipropylene glycol; ketones such as isophorone and trimethylcyclohexanone (dihydroisophorone); and the acetate products such as hexyl or heptyl acetate. The preferred organic liquids are xylene, alkyl substituted benzenes, such as propyl benzene fractions, and alkyl naphthalene fractions.

In general, the amount of solvent employed, if desired, is typically from about 40, preferably from about 50 to about 70, preferably to about 60 weight percent, based on the total weight of a (trichloromethyl)pyridine/solvent solution. The amount of (trichloromethyl)pyridine within a (trichloromethyl)pyridine/solvent solution is typically from about 30, preferably from about 40 to about 60, preferably to about 50 weight percent, based on the weight of a (trichloromethyl)pyridine/solvent solution.

The microcapsules useful in the present invention can be prepared by the polycondensation reaction of a polymeric isocyanate and a polyamine to form a polyurea shell. Methods of microencapsulation are well known in the art and any such method can be utilized in the present invention to provide the capsule suspension formulation. In general, the capsule suspension formulation can be prepared by first mixing a polymeric isocyanate with a (trichloromethyl)pyridine/solvent solution. This mixture is then combined with an aqueous phase which includes an emulsifier to form a two phase system. The organic phase is emulsified into the aqueous phase by shearing until the desired particle size is achieved. An aqueous crosslinking polyamine solution is then added dropwise while stirring to form the encapsulated particles of (trichloromethyl)pyridine in an aqueous suspension.

The desired particle size and cell wall thickness will depend upon the actual application. The microcapsules typically have a volume median particle size of from about 1 to about 10 microns and a capsule wall thickness of from about 10 to about 125 nanometers. In one embodiment, wherein the formulation of the present invention will be incorporated immediately into a growth medium, the desired particle size may be from about 2 to about 10 microns, with a cell wall of from about 10 to about 25 nanometers. In another embodiment, requiring soil surface stability, the desired particle size may be from about 1-5 microns, with cell wall thicknesses of from about 75 to about 125 nanometers.

Other conventional additives may also be incorporated into the formulation such as emulsifiers, dispersants, thickeners, biocides, pesticides, salts and film-forming polymers.

Dispersing and emulsifying agents include condensation products of alkylene oxides with phenols and organic acids, alkyl aryl sulfonates, polyoxyalkylene derivatives of sorbitan esters, complex ether alcohols, mahogany soaps, lignin sulfonates, polyvinyl alcohols, and the like. The surface-active agents are generally employed in the amount of from about 1 to about 20 percent by weight of the microcapsule suspension formulation.

The ratio of the suspended phase to the aqueous phase within the microcapsule suspension formulation of the present invention is dependent upon the desired concentration of (trichloromethyl)pyridine compound in the final formulation. Typically the ratio will be from about 1:0.75 to about 1:100. Generally the desired ratio is about 1:1 to about 1:7, and is preferably from about 1:1 to about 1:4.

The presence of a (trichloromethyl)pyridine compound suppresses the nitrification of ammonium nitrogen in the soil or growth medium, thereby preventing the rapid loss of ammonium nitrogen originating from nitrogen fertilizers, organic nitrogen constituents, or organic fertilizers and the like.

Generally, the microcapsule suspension formulation of the present invention is applied such that the (trichloromethyl)pyridine compound is applied to the soil or a growth medium at a rate of from about 0.5 to about 1.5 kg/hectare, preferably at a rate of from about 0.58 to about 1.2 kg/hectare. The preferred amount can be easily ascertained by the application preference, considering factors such as soil pH, temperature, soil type and mode of application.

The microcapsule suspension formulation of the present invention can be applied in any manner which will benefit the crop of interest. In one embodiment the microcapsule suspension formulation is applied to growth medium in a band or row application. In another embodiment, the formulation is applied to or throughout the growth medium prior to seeding or transplanting the desired crop plant. In yet another embodiment, the formulation can be applied to the root zone of growing plants.

Additionally, the microcapsule suspension formulation can be applied with the application of nitrogen fertilizers. The formulation can be applied prior to, subsequent to, or simultaneously with the application of fertilizers.

The microcapsule suspension formulation of the present invention has the added benefit that it can be applied to the soil surface, without additional water or mechanical incorporation into the soil for days to weeks. Alternatively, if desired, the formulation of the present invention can be incorporated into the soil directly upon application.

The microcapsule suspension formulation of the present invention typically has a concentration of (trichloromethyl)pyridine compound in amounts of from about 1, preferably from about 10 and more preferably from about 15 to about 50 typically to about 35, preferably to about 30 and more preferably to about 25 percent by weight, based on the total weight of the microcapsule suspension formulation, the preferred range is between about 5 to about 40 weight percent nitrapyrin. The microcapsule suspension formulation is then mixed with a solvent or water to obtain the desired rate for application.

Soil treatment compositions may be prepared by dispersing the microcapsule suspension formulation in fertilizers such as ammonium or organic nitrogen fertilizer. The resulting fertilizer composition may be employed as such or may be modified, as by dilution with additional nitrogen fertilizer or with inert solid carrier to obtain a composition containing the desired amount of active agent for treatment of soil.

The soil may be prepared in any convenient fashion with the microcapsule suspension formulation of the present invention, including mechanically mixed with the soil; applied to the surface of the soil and thereafter dragged or diced into the soil to a desired depth; or transported into the soil such as by injection, spraying, dusting or irrigation. In irrigation applications, the formulation may be introduced to irrigation water in an appropriate amount in order to obtain a distribution of the (trichloromethyl)pyridine compound to the desired depth of up to 6 inches (15.24 cm.).

Surprisingly, once incorporated into the soil, the microcapsule suspension formulation of the present invention outperforms other nitrapyrin formulations, especially unencapsulated versions. It was thought that the encapsulated composition would not release nitrapyrin sufficiently to be as effective as the non-encapsulated versions, wherein the diffusion from the capsule would be too slow to provide a biological effect, but in fact the opposite effect is observed.

Due to the controlled release of nitrapyrin in the microcapsule suspension formulation of the present invention, several advantages can be attained. First, the amount of nitrapyrin can be reduced since it is more efficiently released into the soil over an extended period of time. Additionally, the microcapsule suspension formulation of the present invention can be applied and left on the surface to be naturally incorporated into the soil, without the need for mechanical incorporation if desired.

In some embodiments of the microcapsule suspension formulation, post addition (i.e. after microcapsule formation) of aromatic solvents to the aqueous phase reduces the rate of crystal formation and/or growth in the aqueous phase at certain temperature storage conditions. In one embodiment, post-addition, aromatic solvents provide superior crystal growth reduction in cold temperature storage conditions. In an exemplary embodiment, such post-addition, aromatic solvents include an oil or oils, and are present in the aqueous phase of the formulation after the formation of the microcapsules. The term "oil" will herein describe solvents that are generally immiscible with water.

In some embodiments, microcapsule suspension formulations already containing crystals of nitrapyrin and without aromatic solvent(s) in the aqueous phase, can be treated with one or more aromatic solvents by addition to the aqueous phase, and the resulting mixture can be stirred at ambient temperature for a length of time, possibly 30 minutes to 5 hours based on the total volume of the microcapsule suspension, until the crystals of nitrapyrin have disappeared.

Without the addition of one or more aromatic solvents to the aqueous phase, the microcapsule suspension formulation of the present application may form nitrapyrin crystals in the aqueous phase at mild cold storage temperatures, about 100 C. The nitrapyrin crystals may be about 99% pure. Over time, such crystals may compose up to 0.5 weight percent of the overall microcapsule suspension formulation. However, crystals may also form at other temperatures, such as 00 C, −50 C, and 150 C. Solvent-based crystal growth inhibitors such as aromatic solvents can provide superior physical stability, particularly at mild cold storage temperatures at about 100 C, to prevent crystal formation in the aqueous phase of the microcapsule suspension.

Illustratively, aromatic solvents that may be added after the formation of the microcapsule suspension include: Aromatic 100 Fluid, also known as solvent naphtha or light aromatic; Aromatic 150 Fluid, also known as solvent naphtha, heavy aromatic, high flash aromatic naphtha type II, heavy aromatic solvent naphtha, hydrocarbons, C10 aromatics, >1% naphthalene, A150, 5150 (Solvesso 150); and Aromatic 200 Fluid, also known as solvent naphtha, heavy aromatic, high flash aromatic naphtha type II, heavy aromatic solvent naphtha, hydrocarbons, C10-13 aromatics, >1% naphthalene, A200, and S200 (Solvesso 200).

In some embodiments the aromatic solvents that may be added to the formulation after the formation of the microcapsule suspension include, are naphthalene depleted, or contain less than about 1% naphthalene. Said solvents can be added to the microcapsule suspension formulation prior to crystal formation as a preventative measure, or added to the microcapsule suspension formulation after crystal formation as a remedial measure to remove or reduce the presence of crystals.

Additionally, the microcapsule suspension formulation of the present invention can be combined or used in conjunction with pesticides, including arthropodicides, bactericides, fungicides, herbicides, insecticides, miticides, nematicides, nitrification inhibitors such as dicyandiamide, urease inhibitors such as N-(n-butyl)thiophosphoric triamide, and the like or pesticidal mixtures and synergistic mixtures thereof. In such applications, the microcapsule suspension formulation of the present invention can be tank mixed with the desired pesticide(s) or they can be applied sequentially.

Exemplary herbicides include, but are not limited to acetochlor, alachlor, aminopyralid, atrazine, benoxacor, bromoxynil, carfentrazone, chlorsulfuron, clodinafop, clopyralid, dicamba, diclofop-methyl, dimethenamid, fenoxaprop, flucarbazone, flufenacet, flumetsulam, flumiclorac, fluroxypyr, glufosinate-ammonium, glyphosate, halosulfuron-methyl, imazamethabenz, imazamox, imazapyr, imazaquin, imazethapyr, isoxaflutole, quinclorac, MCPA, MCP amine, MCP ester, mefenoxam, mesotrione, metolachlor, s-metolachlor, metribuzin, metsulfuron methyl, nicosulfuron, paraquat, pendimethalin, picloram, primisulfuron, propoxycarbazone, prosulfuron, pyraflufen ethyl, rimsulfuron, simazine, sulfosulfuron, thifensulfuron, topramezone, tralkoxydim, triallate, triasulfuron, tribenuron, triclopyr, trifluralin, 2,4-D, 2,4-D amine, 2,4-D ester and the like Exemplary insecticides include, but are not limited to 1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfiram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

Additionally, any combination of the above pesticides can be used.

Additionally, Rynaxypyr™, a new crop protection chemistry from DuPont with efficacy in controlling target pests can be used.

As used throughout the specification, the term "about" refers to plus or minus 10% of the stated value, for example the term 'about 1.0' includes values from 0.9 to 1.1.

The following examples are provided to illustrate the present invention. The examples are not intended to limit the scope of the present invention and they should not be so interpreted. Amounts are in weight parts or weight percentages unless otherwise indicated.

EXAMPLES

Capsule Suspension Preparation

The weight percentages of the components for capsule suspension preparation are summarized in Table I. Total batch size is based on the weight of nitrapyrin used which is typically approximately 25 g. The emulsifiers and crosslinking amines are added as aqueous solutions of the indicated concentrations. Microcapsule suspension formulation techniques are known in the art. Additionally, it is also well known in the art that the order of addition and corresponding procedures for producing microcapsule suspension formulations may produce formulations having varying physical characteristics such as viscosity. The following preparation procedure is one illustrative embodiment of preparation procedures, and should not be considered as limiting this invention.

Oil soluble monomer PAPI 27 (polymethylene polyphenylisocyanate) (Dow Chemical), is added to a wide-mouthed jar. Nitrapyrin (Dow AgroSciences) and Aromatic 200 (Exxon) are then added in the form of a 50% nitrapyrin stock solution. The resulting organic phase is combined with an aqueous solution of the emulsifier(s) as indicated in Table I. The resulting two-phase mixture is emulsified using a Silverson L4RT-A high-speed mixer fitted with the ¾ in. mixing tube and general purpose emulsification head. Emulsification is achieved by first mixing at relatively low speed (~1000 rpm) with the end of the mixing tube located in the aqueous phase to draw in the organic phase until well emulsified. The speed is then increased in discrete increments, measuring the particle size after each increase. This process is continued until the desired particle size is obtained. The water-soluble amine (diethylenetriamine (DETA, Aldrich) or ethylenediamine (EDA, Aldrich) solution (10 wt. % in water) is then added dropwise while stirring at a reduced rate. Following the completion of the addition the resulting capsule suspension is stirred for an additional minute. Following capsule formation, Kelzan S (as 1.5% aqueous solution), Veegum (as 5% aqueous solution), Proxel GXL and the balance of the water were added as indicated in Table I and a final homogenization was performed with the Silverson mixer.

TABLE I

Principle Components Of Exemplary Compositions 1, 2, 3, 4, 5, 6, and 7.

| Material | Weight Percent | | | | | | |
| --- | --- | --- | --- | --- | --- | --- | --- |
| | Ex. 1 | Ex. 2 | Ex. 3 | Ex. 4 | Ex. 5 | Ex. 6 | Ex. 7 |
| Nitrapyrin | 9.46 | 9.47 | 9.45 | 9.47 | 9.45 | 9.35 | 12.76 |
| Aromatic 200 | 9.46 | 9.47 | 9.45 | 9.47 | 9.45 | 9.35 | 15.22 |
| Dispersant/ Emulsifier | 0.96[1] (added as 5% aq. sol'n) | 0.48[1] (added as 2.5% aq. sol'n) | 0.97[1] (added as 5% aq. sol'n) | 0.48[1] (added as 2.5% aq. sol'n) | 1.94[1] (added as 10% aq. sol'n) | 2.43[1] (added as 10% aq. sol'n) | 1.98[4] (added as 5% aq. sol'n) |
| Thickener[2] | 0.15 | 0.15 | 0.15 | 0.15 | 0.15 | 0.15 | 0.02 |
| Emulsifier | | | | | | | 0.99[5] |
| Suspending Aid | | | | | | | 0.2[6] |
| PAPI-27 | 0.18 | 0.09 | 0.47 | 0.23 | 0.47 | 5.61 | 9.13 |
| Amine | 0.04[7] | 0.02[7] | 0.11[7] | 0.06[7] | 0.13[8] | 1.35[7] | 2.19[7] |
| Biocide[3] | 0.1 | 0.1 | 0.1 | 0.1 | 0.1 | 0.1 | 0.1 |
| Total Water | 79.65 | 80.22 | 79.30 | 80.04 | 78.31 | 71.68 | 57.40 |

TABLE I-continued

Principle Components Of Exemplary Compositions 1, 2, 3, 4, 5, 6, and 7.

| Material | Weight Percent | | | | | | |
|---|---|---|---|---|---|---|---|
| | Ex. 1 | Ex. 2 | Ex. 3 | Ex. 4 | Ex. 5 | Ex. 6 | Ex. 7 |
| Calculated Density | 1.057 | 1.056 | 1.058 | 1.056 | 1.059 | 1.070 | 1.097 |

[1]Gohsenol GL-03 (polyvinyl alcohol available from Nippon Gohsei)
[2]Kelzan S-Xanthan gum (available from CP Kelco)
[3]Proxel GXL (1,2-Benzisothiazol-3(2H)-one available from Arch Chemicals, Inc.)
[4]Kraftsperse 25M (available from MeadWestvaco)
[5]Tergitol 15-S-7 (available from The Dow Chemical Company)
[6]Veegum (hectorite clay) (available from R. T. Vanderbilt Co., Inc.)
[7]EDA—ethylenediamine (available from Aldrich)
[8]DETA—diethylenetriamine (available from Aldrich)

Particle Size Measurement of Capsules

Capsule suspension particle size distributions are determined using a Malvern Mastersizer 2000 light scattering particle sizer fitted with a small volume sample unit. The volume median distribution ("VMD") is reported for each formulation in Table II.

TABLE II

Particle Size and Cell Wall Thickness

| Example | Particle size (μm) | Thickness (nm) | amine |
|---|---|---|---|
| 1 | 5 | 10 | EDA |
| 2 | 10 | 10 | EDA |
| 3 | 5 | 25 | EDA |
| 4 | 10 | 25 | EDA |
| 5 | 2 | 10 | DETA |
| 6 | 2 | 100 | EDA |
| 7 | 2 | 100 | EDA |

Concentration of nitrapyrin is 100 g/L except for the formulation of Example 7 which is 140 g/l in the formulation based on the calculated density in Table I.
EDA—ethylenediamine
DETA—diethylenetriamine Calculation of Wall Thickness The calculation of the amounts of capsule wall components needed to achieve a target wall thickness is based on the geometric formula relating the volume of a sphere to its radius. If a core-shell morphology is assumed, with the core comprised of the non wall-forming, water insoluble components (nitrapyrin, solvent) and the shell made up of the polymerizable materials (oil- and water-soluble monomers), then equation (1) holds, relating the ratio of the volume of the core ($V_c$) and the volume of the core plus the volume of the shell ($V_s$) to their respective radii, where $r_s$ is radius of the capsule including the shell and $l_s$ is thickness of the shell.

$$\frac{V_c + V_s}{V_c} = \left(\frac{r_s}{r_s - l_s}\right)^3 \quad (1)$$

Solving equation (1) for the volume of the shell yields:

$$V_s = V_c\left(\left(\frac{r_s}{r_s - l_s}\right)^3 - 1\right) \quad (2)$$

Substituting masses ($m_i$) and densities ($d_i$) for their respective volumes ($m_s/d_s = V_s$ and $m_c/d_c = V_c$, where the subscript s or c refers to the shell or core, respectively) and solving for the mass of the shell gives:

$$m_s = m_c \frac{d_s}{d_c}\left(\left(\frac{r_s}{r_s - l_s}\right)^3 - 1\right) \quad (3)$$

It can be seen by comparing equations (2) and (3) that the effect of the density ratio $d_s/d_c$ is to apply a constant correction factor when masses are used to calculate the amounts of wall components needed to produce a capsule of desired size and wall thickness. To be rigorous in the calculation of $m_s$, therefore, the densities of the core and shell must be known or at least estimated from the weighted averages of the densities of each of the components. However, the primary purpose of these calculations is to use capsule wall thickness as a convenient conceptual tool which would hopefully be helpful in understanding capsule performance behavior and, therefore, in designing new capsule formulations. Approximate values are felt to be sufficient for this purpose. With this in mind the simplification is made of setting the value of $d_s/d_c$ to 1, which yields equation (4).

$$m_s \approx m_c\left(\left(\frac{r_s}{r_s - l_s}\right)^3 - 1\right) \quad (4)$$

Making the substitutions $m_c = m_o - m_{OSM}$, $m_s = m_o + (f_{WSM/OSM})m_{OSM} - m_c$, and $f_{WSM/OSM} = m_{WSM}/m_{OSM}$ (the ratio of water soluble monomer to oil soluble monomer), where $m_o$ is the total mass of the oil components (nitrapyrin, solvent, oil-soluble monomer), $m_{OSM}$ is the mass of the oil-soluble monomer, and $m_{WSM}$ is the mass of the water-soluble monomer, and solving for $m_{OSM}$ yields:

$$m_{OSM} = \frac{m_o\left(\left(\frac{r_s}{r_s - l_s}\right)^3 - 1\right)}{f_{WSM/OSM} + \left(\frac{r_s}{r_s - l_s}\right)^3} \quad (5)$$

For the determination of mOSM, the entire quantity of mWSM is used in the calculation. In the present study the water-soluble monomer is used at a 1:1 equivalent weight relative to the oil-soluble monomer for all of the capsule suspension preparations.

Conversely, the capsule wall thickness ls is calculated for each of the capsule suspension preparations using the VMD particle size for the value of $r_s$ and equation (6). These values are included in Table II.

$$l_s = \frac{r_s\left(\left(\frac{m_O + f_{WSM/OSM}m_{OSM}}{m_O - m_{OSM}}\right)^{\frac{1}{3}} - 1\right)}{\left(\frac{m_O + f_{WSM/OSM}m_{OSM}}{m_O - m_{OSM}}\right)^{\frac{1}{3}}} \quad (6)$$

Testing the Efficacy of Exemplary Compositions, 1, 2, 3, 4, and 5

A bulk sample of Drummer silty clay loam (sicl) soil is collected, air-dried and crushed to pass a 2-mm screen. Following the soil preparation, approximately 25 grams of the processed soil is placed into beakers and treated with 7.5 ml water containing 10 mg N (as $(NH_4)_2SO_4$) and 0.0, 0.25 or 0.50 ppm nitrapyrin (based on the weight of soil sample) using each of the Example formulations 1-5. The treated soil is then evenly distributed over the soil surface and immediately covered with another 25 grams of soil. Three replications at each rate are provided as well as three 50 gram soil samples without fertilizer or inhibitor addition and three replications of N-Serve 24 (Dow AgroSciences) treated soil. Once liquid is absorbed into soil, the materials are mixed to attain even distribution of the fertilizer/Example formulation. After mixing, water is added to bring soil to field capacity. Beakers are unsealed, but covered to reduce evaporation and maintained at room temperature, approximately 25° C. The amount of water lost from each beaker is measured at 5-day intervals and replaced if the loss exceeds 2.5 ml.

On day 7, 14, 21, 28, 35, 42, 49, and 56 after initiation of the incubation, the soil contained in each individual beaker is dried, ground, and mixed. A subsample is analyzed for NH4-N, as described by Mulvaney, R. L. 1996; "Nitrogen-Inorganic Forms", pp. 1123-1184. In D. L. Sparks (ed.) Methods of soil analysis: Part 3/SSSA Book Ser.5.SSSA, Madison, Wis. If less than 30% of the N remains as ammonium in all replications of any treatment, analysis of that treatment is ceased. Averages of the replications are provided in Table III and Table IV.

TABLE III 0.5 ppm Nitrapyrin

| Example | PPM NH$_4$ | | | | |
|---|---|---|---|---|---|
| | Week 1 | Week 2 | Week 3 | Week 4 | Week 5 |
| No inhibitor Control | 82.7 | 74.3 | 54.8 | 38.5 | 24.3 |
| 1 | 82.3 | 84.2 | 67.7 | 59.6 | 48.9 |
| 2 | 82.5 | 79.5 | 71.3 | 63.1 | 49.8 |
| 3 | 81.8 | 78.8 | 67.6 | 64.3 | 46.7 |
| 4 | 88.5 | 81.8 | 77.5 | 55.6 | 46.1 |
| 5 | 82.9 | 78.0 | 70.8 | 57.0 | 51.7 |
| N-Serve 24 | 87.1 | 75.5 | 64.9 | 55.6 | 37.4 |

TABLE IV 0.25 ppm Nitrapyrin

| Example | PPM NH$_4$ | | | | |
|---|---|---|---|---|---|
| | Week 1 | Week 2 | Week 3 | Week 4 | Week 5 |
| No inhibitor Control | 82.7 | 74.3 | 54.8 | 38.5 | 24.3 |
| 1 | 83.2 | 79.6 | 68.0 | 57.3 | 43.9 |
| 2 | 82.6 | 78.4 | 64.7 | 53.6 | 42.4 |

TABLE IV-continued 0.25 ppm Nitrapyrin

| Example | PPM NH$_4$ | | | | |
|---|---|---|---|---|---|
| | Week 1 | Week 2 | Week 3 | Week 4 | Week 5 |
| 3 | 81.4 | 73.8 | 61.1 | 50.7 | 37.9 |
| 4 | 78.5 | 72.6 | 60.3 | 48.5 | 37.3 |
| 5 | 83.5 | 78.1 | 61.0 | 48.0 | 35.1 |
| 0.5 N-Serve 24 | 87.1 | 75.5 | 64.9 | 55.6 | 37.4 |

The microencapsulated formulations are compared to the nitrapyrin N-Serve 24 (available from Dow AgroSciences) formulation at the same rate. At Week 5 all five encapsulated formulations tested in using 0.5 ppm Nitrapyrin are outperforming N-Serve 24, demonstrating that at the same rate they provide superior residual nitrogen-stabilizing performance.

Exemplary Compositions 6 and 7 Include an Ionic Stabilizer

The aqueous phases of Exemplary compositions 6 and 7 further include an ionic stabilizer. In these compositions the ionic stabilizer is sodium dioctylsulphosuccinate (Geropon SDS, available from Rhodia) was used. Any other suitable ionic stabilizer may be used instead of or in addition to sodium dioctylsulphosuccinate.

Four replications of Exemplary compositions 6 and 7, and N-Serve 24 (0.5 lb a.i./acre; 0.58 kg/hectare) in combination with urea ammonium nitrate (UAN) (160 lb/acre; 181.5 kg/hectare), as well as four replications of urea ammonium nitrate (160 lb N/acre; 181.5 kg/hectare) with 0 nitrification inhibitor treatment are applied to Drummer sicl samples clear of vegetation.

Following application of the example formulations, the formulations are incorporated immediately with moisture. Once incorporation occurs, treatments are open to native rainfall and environmental effects.

Soil samples are collected from each treatment and analyzed for $NH_4$—N as described by Mulvaney, as referenced previously, at 21, 28, 35, 42, 49 and 56 days after incorporation. Samples are collected from 0-3 inch (0-7.6 cm), depths for 8 weeks with additional samples collected from a 3-6 inch (7.6 cm-15.2 cm) depth in weeks 7 and 8 after the first treatment is incorporated. On the day of application, samples are collected from the 0-3 inch (0-7.6 cm) depth for $NH_4$—N analysis.

The effectiveness of a nitrification inhibitor to keep nitrogen in the ammonia form is measured by analyzing soil samples for the presence of the ammonium molecule ($NH_4$). Averages of the replications are reported in Table V.

TABLE V

Level of NH$_4$ in the Soil Were Measured for the Controls and Exemplary Compositions 6 and 7

| Example | PPM NH$_4$ | | | | | | |
|---|---|---|---|---|---|---|---|
| | Week 3 | Week 4 | Week 5 | Week 6 | Week 7 | Week 8 | Week 9 |
| N-Serve-24 Comparison | 27.4 | 15.6 | 10.2 | 12.6 | 8.3 | 4.2 | 7.0 |
| UAN Control | 16.7 | 13.3 | 5.3 | 7.0 | 7.2 | 4.0 | 5.0 |
| Example 6 | 24.9 | 19.2 | 8.5 | 10.2 | 6.6 | 3.6 | 5.5 |
| Example 7 | 26.4 | 22.0 | 16.3 | 12.4 | 9.1 | 5.8 | 6.0 |

UAN—Urea ammonium nitrate

In a further analysis, the nitrification inhibition of Examples 6 and 7 are coupled with the surface stability of those formulations. The UAN alone and the UAN+N-Serve treatments are moisture incorporated on the day of application to the soil while the two example formulations lay on the soil surface for a week prior to incorporation. Plots awaiting moisture incorporation are protected from moisture when rain events are threatening. Results are listed in TABLE VI.

TABLE VI

Delayed Incorporation Determined Using Exemplary Compositions 6 and 7 and Controls

| | PPM $NH_4$ | | | | | | | |
|---|---|---|---|---|---|---|---|---|
| Examples | week 2 | week 3 | week 4 | week 5 | week 6 | week 7 | week 8 | week 9 |
| N-Serve-24 Comparison | 42.3 | 35.1 | 24.6 | 18.8 | 30.0 | 17.2 | 19.4 | 24.4 |
| UAN Control | 48.4 | 34.9 | 22.8 | 16.2 | 26.7 | 15.4 | 21.5 | 19.0 |
| Example 6 | 50.6 | 41.6 | 30.2 | 22.4 | 34.0 | 18.6 | 27.0 | 28.5 |
| Example 7 | 54.0 | 55.6 | 39.1 | 40.9 | 40.0 | 25.6 | 31.4 | 34.4 |

Referring now to Tables V and VI. Both Exemplary compositions 6 and 7 are more effective nitrification inhibitor than is N-Serve 24.

Preparations and Components of Exemplary Compositions 8 and 9

The weight percentages of the components used for capsule suspension preparation for exemplary compositions are listed in Table VII. Total batch size is 2.1 kg (Examplary composition 8) or 185 g (Examplary composition 9). Oil soluble monomer PAPI 27 (polymethylene polyphenylisocyanate, Dow Chemical), is added to a wide-mouthed jar. N-Serve TG (Dow AgroSciences; 90 wt % nitrapyrin) and Aromatic 200 (Exxon) are then added in the form of a nitrapyrin technical concentrated stock solution. The resulting homogeneous organic phase is combined with an aqueous solution composed of Kraftsperse 25M, Tergitol 15-S-7, Geropon SDS, and Proxcel GXL.

The resulting two-phase mixture is emulsified using a Silverson L4RT-A highspeed mixer fitted with the ⅝ in. mixing tube and general purpose emulsification head. Emulsification is achieved by first mixing at relatively low speed (~1000 rpm) with the end of the mixing tube located in the aqueous phase to draw in the organic phase until well emulsified. The speed is then increased in discrete increments, measuring the particle size after each increase. This process is continued until the desired particle size (2.5 micron) is obtained.

Next the water-soluble amine ethylenediamine aqueous solution (20 wt % in example 8; 30 wt % in Exemplary compositions 9, 10, and 11) is added drop wise while the mixture is stirred at a reduced rate. Following the addition of the water-soluble amine resulting capsule suspension is stirred for an additional period of time in order to allow the polyurea shell forming reaction to run further towards completion. Following capsule formation, the finishing phase includes adding Avicel (as 5 wt % aqueous solution, Kelzan (as 1.5 wt % aqueous solution), Proxel GXL and the balance of the water as indicated in Table VII and a final homogenization was performed with the Silverson mixer. The dispersed phase, including nitrapyrin, aromatic 200, PAPI 27, and ethylenediamine, is 49.55 wt % (example 8) or 55.94 wt % (example 9).

Preparation and Components of Exemplary Composition 10

The weight percentages of the components for capsule suspension preparation are listed in Table VII. Total batch size is 100 kilograms. A homogenous solution of N-Serve TG (Dow AgroSciences, 90 wt % nitrapyrin) and Aromatic 200 (Exxon) is prepared by melting N-Serve TG and adding it to the solvent. To this, the oil soluble monomer PAPI 27 is added and mixed together to create the Oil Phase. The Aqueous Phase is prepared by mixing Kraftsperse 25M, Tergitol15-S-7, Geropon SDS, Proxel GXL, Antifoam 100 IND and water into a homogeneous solution.

The Oil Phase and Aqueous Phase are metered together in a 1.25:1.0 ratio through a rotor/stator homogenizer cell to create an emulsion of the desired particle size (2.5 micron). This process continues until the oil phase is depleted. The batch is cooled down to below 15° C. before the amine is added. The 30 weight % amine is added into the batch under agitation. The reaction vessel is stirred for a minimum of 2 hours before the viscosity components are added. The viscosity phase consists of 5 w/w % A vicel, 1.5 w/w % Kelzan S, 1% Proxel GXL and water. Additional water is added if necessary to achieve the target assay, then the batch is packaged for final use.

Preparation and Components of Exemplary Composition 11

The weight percentages of the components for used to prepare the capsule suspension in Exemplary composition are listed in Table VII. The total batch size is 400 kilograms. A homogenous solution of N-Serve TG (Dow AgroSciences, 90 wt % nitrapyrin) and Aromatic 200 (Exxon) is prepared by melting N-Serve TG and adding it to the solvent. To this, the oil soluble monomer PAPI 27 is added and mixed together to create the Oil Phase. The Aqueous Phase is prepared by mixing Kraftsperse 25M, Tergitol15-S-7, Geropon SDS, Proxel GXL, Antifoam 100 IND and water into a homogeneous solution.

The Oil Phase and Aqueous Phase are metered together in a 1.25:1.0 ratio through a rotor/stator homogenizer cell to create an emulsion of the desired particle size (2.5 micron). This process continues until the oil phase is depleted. The batch is cooled down to below 15° C. before the amine is added. The 30 weight % amine is added into the batch by using a side stream circulation stream pumping the emulsion at a rate of 100 liters per minute. The amine is added in less than 10 minutes, preferably less than 5 minutes, to set the capsules walls. The reaction vessel is stirred for a minimum of 2 hours before the viscosity components are added. The viscosity phase consists of 5 w/w % A vicel, 1.5 w/w % Kelzan S, 1% Proxel GXL and water. Additional water is added if necessary to achieve the target assay, then the batch is packaged for final use.

TABLE VII

Principle Components of Exemplary Compositions 8, 9, 10, and 11

| | Weight Percent (wt %) | | | |
|---|---|---|---|---|
| Material | Example 8 | Example 9 | Example 10 | Example 11 |
| N-Serve TG | 19.78 | 23.68 | 19.63 | 19.63 |
| Aromatic 200 | 18.91 | 22.65 | 18.78 | 18.78 |
| PAPI-27 | 8.87 | 7.72 | 8.80 | 8.80 |
| Dispersant[1] | 1.19 | 1.18 | 1.18 | 1.18 |
| Emulsifier[2] | 1.19 | 1.18 | 1.18 | 1.18 |
| Ionic Stabilizer[3] | 0.24 | 0.24 | 0.24 | 0.24 |
| Antifoam[4] | | 0.09 | 0.09 | 0.09 |
| Biocide[5] | 0.12 | 0.12 | 0.12 | 0.12 |
| Amine[6] | 1.99[a] | 1.90[b] | 1.97[c] | 2.17[c] |
| Suspending Aid[7] | 0.19 | 0.22 | 0.19 | 0.19 |

TABLE VII-continued

Principle Components of Exemplary Compositions 8, 9, 10, and 11

| | Weight Percent (wt %) | | | |
|---|---|---|---|---|
| Material | Example 8 | Example 9 | Example 10 | Example 11 |
| Thickener[8] | | | 0.03 | 0.03 |
| Total Water | 47.52 | 41.02 | 47.79 | 47.59 |

[1]Kraftsperse 25M (available from MeadWestvaco)
[2]Tergitol 15-S-7 (available from The Dow Chemical Company)
[3]Geropon SDS (sodium dioctylsulphosuccinate available from Rhodia)
[4]Antifoam 100 IND (available from Harcros Chemicals Inc.)
[5]Proxel GXL (1,2-Benzisothiazol-3(2H)-one available from Arch Chemicals, Inc.)
[6]EDA—ethylenediamine (available from Aldrich) in
 [a]20 wt %;
 [b]50 wt %; and
 [c]30 wt % aqueous solution
[7]Avicel (available from FMC Biopolymer)
[8]Kelzan S-Xanthan gum (available from CP Kelco)

Determining the Effect of Adding an Aromatic Solvent to the Aqueous Phase of the Suspension after the Formation of the Microcapsule in the Suspension Portions (~195 grams suspension formulation) of a microcapsule suspension formulation of the present disclosure were weighed into 250 mL glass bottles. Specific amounts (based on weight percent) of various aromatic solvents were added directly into the glass bottles containing the microcapsule suspension formulations.

The bottles were agitated on a linear shaker for 30-45 minutes to prepare uniform microcapsule suspension formulations, i.e. to dissolve or disperse the post-added aromatic solvents throughout the microcapsule suspension formulation. Once a homogeneous formulation was achieved, sample bottles were placed in a refrigerator at about 0° C. or at about 10° C. Each bottle was sampled at various time points and the sample were tested for the presence of crystals in the aqueous phase.

A wet sieve procedure was carried out in order to determine the crystal formation as a weight percentage of the total microcapsule suspension formulation in the 10° C. and 0° C. storage samples. Approximately 20 grams of a sample of each individual microcapsule suspension formulation were added to a glass beaker containing between 100 and 200 grams of tap water. The solution was stirred using a glass stir rod and then poured through a 75 μm mesh sieve. The beaker was rinsed with additional water and the rinse was also being poured through the sieve. Tap water was poured over the sample in the sieve for approximately 30 seconds to rinse weak agglomerates through the filter. The residual left on the screen was rinsed onto a tared filter paper and vacuum filtered. This filter paper with sample was allowed to dry in a vacuum hood for at least four hours and then reweighed. Residue percentages were calculated using the equation as follows: Residue Percentage (%)=(Filter paper and Residue Weight After Drying (g)−Filter paper Weight (g))/(Total Sample Sieved (g)). Nitrapyrin crystals isolated from the microcapsule suspension formulations were analyzed for chemical identification and purity by gas chromatography using an internal standard technique.

The process was repeated for each sample stored at 10° C. and 0° C. at 2-week and 4-week time intervals and residue weight percentages were recorded as listed in Table VIII below. The screening results shown in Table VIII show that Aromatic 200ND (naphthalene depleted) significantly reduced crystal formation and improved crystallization stability after 4 weeks of storage at 10° C. and 0° C., as compared to the control wherein no crystal inhibitor was added.

TABLE VIII

A list of putative solvent based crystal inhibitors, which were added to the microcapsule suspensions after the formation of the microcapsules. Suspensions including the putative solvents (and control formulations) were stored at 10° C. and 0° C. and assayed for the presence of crystals in the aqueous phase. All samples which included putative crystal inhibitors were tested against a control microcapsule suspension formulation which did not include any putative crystal inhibitors. (Trace: ≤0.001%).

| Post added Solvent Conc. in Microcapsule Suspension Formulation | Wet Sieve, 75 micron, weight percent | | | | | Observations |
|---|---|---|---|---|---|---|
| | Initial | 2 weeks 0° C. | 2 weeks 10° C. | 4 weeks 0° C. | 4 weeks 10° C. | |
| [1]Microcapsule Suspension Formulation Control | Trace | Trace | Trace | 0.010 | 0.240 | Needle crystals |
| Cyclohexanone, 2.86% | Trace | Trace | Trace | 1.17 | 0.028 | Needle crystals |
| [2]Hallcomid M-8-10, 2.86% | Trace | 0.120 | Trace | 1.46 | 0.025 | Long needle crystals |
| Aromatic 200ND, 2.86% | Trace | Trace | Trace | Trace | Trace | No significant crystals |

[1]No added solvent-based crystal inhibitors
[2]HALLCOMID M-8-10 is a [N,N-dimethyloctanamide (N,N-dimethylcaprylamide) and N,N-dimethyldecanamide (N,N-dimethylcapramide)]. CAS Reg. No. 1118-92-9, 14433-76-2.

Referring to Table, VIII. As evidenced by the lack of crystals in the aqueous phase, after storage for 4 weeks stored at 0° C. and 10° C. Aromatic 200ND showed the best results. Cyclohexanone and Hallcomid M-8-10 did not perform as well as the Aromatic 200ND. Actually, Table VIII shows that after being stored for 4 weeks for 0° C., the amount of the crystals of nitrapyrin (based on weight percent) increased in samples prepared using the putative crystallization inhibitors cyclohexanone and Hallcomid M-8-10 relative to the control group which included no additional solvents added to the aqueous phase of the suspensions.

These results are surprising given that cyclohexanone is known as a particularly effective solvent for nitrapyrin (dissolving at ambient temperature (24° C.) about 60 wt % nitrapyrin). Cyclohexanone is also known to dissolve more nitrapyrin at ambient temperature (24° C.) than Aromatic 100, which dissolves only about 51 weight percent nitrapyrin at ambient temperature (24° C.).

In addition, Hallcomid M-8-10 is known to dissolve about 50 weight percent nitrapyrin at ambient temperature, about 40 weight percent at 0° C., and about 35 weight percent at −10° C. While, Aromatic 150 dissolves only about 43 weight percent nitrapyrin at ambient temperature, about 25 weight percent at 0° C., and about 29 weight percent at −10° C.

Based on its similarity to Aromatic 100 and 150, Aromatic 200ND was expected to perform at about the same level of other aromatic solvents as far as dissolving or reducing nitrapyrin crystals (i.e. less successfully than either cyclohexanone or Hallcomid M-8-10). As the results summarized in Table VIII indicate, Aromatic 200ND proved to be an unexpectedly better inhibitor or crystal formation and the other solvents tested in this experiment.

Testing the Ability of Aromatic 200 to Prevent Nitrapyrin Crystal Formation in the Aqueous Phase of Microcapsule Suspensions Microcapsule suspension formulations with oil phases containing 44.7%, 47.1% and 49.1% Nitrapyrin in Aromatic 200 were prepared. See Table IX for a listing of the components in each formulation. Samples from each formulation were placed in bottles and the bottles were stored in refrigerator, the refrigerator was maintained at about 10° C. Each bottle was sampled at different times, and each sample was tested for the presence of crystals formation using the wet sieve test.

TABLE IX

Microcapsule formulations prepared with Nitrapyrin in Aromatic 200 oil phases containing 44.7%, 47.1%, and 49.1% Nitrapyrin. Wet sieve results after storage at 10° C. All samples tested against a control microcapsule formulation (Nitrapyrin in Aromatic 200 oil phase containing 47.1% Nitrapyrin) with 2.00% post encapsulation Aromatic 200 addition. Microcapsule Suspension Preparation Condition

| Column 1 | Column 2 | Column 3 | Column 4 | Column 5 |
| --- | --- | --- | --- | --- |
| Nitrapyrin % in Oil Phase | 44.7 | 47.1 | 49.1 | 47.1 |
| Aromatic 200 Post Encapsulation Addition | No | No | No | 2.00% |

| Material | Composition Weight Percent (wt %) | | | |
| --- | --- | --- | --- | --- |
| N Serve TG (90.1% Nitrapyrin) | 19.82 | 19.82 | 19.82 | 19.43 |
| Aromatic 200 in Oil Phase | 20.12 | 18.12 | 16.12 | 17.76 |
| Aromatic 200 in Aqueous Phase | 0.00 | 0.00 | 0.00 | 1.96 |
| PAPI-27 | 8.63 | 8.63 | 8.63 | 8.46 |
| Dispersant 11 | 1.17 | 1.17 | 1.17 | 1.15 |
| Emulsifier2 | 1.16 | 1.16 | 1.16 | 1.14 |
| Ionic Stabilizer3 | 0.12 | 0.12 | 0.12 | 0.12 |
| Antifoam4 | 0.08 | 0.08 | 0.08 | 0.08 |
| Biocide5 | 0.12 | 0.12 | 0.12 | 0.12 |
| Amine6 | 2.16 | 2.16 | 2.16 | 2.11 |
| Suspending Aid7 | 0.20 | 0.20 | 0.20 | 0.20 |
| Thickener8 | 0.08 | 0.08 | 0.08 | 0.08 |
| Antifreeze9 | 7.88 | 7.88 | 7.88 | 7.72 |
| Dispersant 210 | 1.51 | 1.51 | 1.51 | 1.49 |
| Total Water | 36.95 | 38.95 | 40.95 | 38.18 |

1Kraftsperse 25M (available from MeadWestvaco)
2Tergitol 15-S-7 (available from The Dow Chemical Company)
3Geropon SDS (sodium dioctylsulphosuccinate available from Rhodia)
4Antifoam 100 IND (available from Harcros Chemicals Inc.)
5Proxel GXL (1,2-Benzisothiazol-3(2H)-one available from Arch Chemicals Inc.)
6EDA—ethylenediamine (available from Aldrich) 30 wt % aqueous solution
7Avicel (available from FMC Biopolymer)
8Kelzan S - Xanthan gum (available from CP Kelco)
9Propylene glycol (available from Aldrich)
10Metasperse 500L (available from Croda Inc.)

The microcapsule formulations prepared with additional Aromatic 200 in the oil phase microcapsule (44.7% Nitrapyrin in the oil phase, 2% additional Aromatic 200 compared to the formulation prepared with 47.1% Nitrapyrin in the oil phase) produced Nitrapyrin crystals after 6 weeks storage at 10° C. In comparison the microcapsule formulation prepared with 47.1% Nitrapyrin in the oil phase and with 2.00% Aromatic 200 post encapsulation addition showed no Nitrapyrin crystal formation after 12 week storage at 10° C. Determining the Effect of Adding Aromatic 200 to a Suspension of Microencapsulated Nitrapyrin which Already Exhibits the Presence of Nitrapyrin Crystals in the Aqueous Phase A microcapsule suspension formulation, similar if not identical to the commercially available formulation Instinct™ (available from Dow AgroSciences) comparable similar to formulation formed by reacting the components of columns 3 or 5 of Table IX, which exhibited included crystals of nitrapyrin in the aqueous phase was treated by adding about 2 wt % Aromatic 200 to the aqueous phase. The resulting mixture was stirred at ambient temperature for 30 minutes to 5 hours. After the mixing no the crystals of nitrapyrin were present in the aqueous phase of the formulation. These results indicate that adding a small portion of Aromatic 200 to the aqueous phase of suspensions of microencapsulated nitrapyrin such as Instinct™ can both prevent the formation of nitrapyrin crystals in the aqueous phase it can also be used to significantly reduce or even eliminate preformed crystals nitrapyrin in the present in the aqueous phase of such suspensions.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

The invention claimed is:

1. A microcapsule suspension formulation, comprising:
    (a) a suspended phase, the suspended phase including a plurality of microcapsules, the microcapsules having a volume median particle size of from about 1 to about 10 microns, wherein the microcapsules comprise:
        (1) a microcapsule wall produced by an interfacial polycondensation reaction between a polymeric isocyanate and a polyamine to form a polyurea shell having a weight percentage of about 0.2 to about 40 percent of a total weight of the microcapsule suspension formulation, and
        (2) a substantially liquid core, the substantially liquid core is encapsulated within the polyurea shell, wherein the substantially liquid core includes about 60 weight percent 2-chloro-6-(trichloromethyl)pyridine of the entire microcapsule and wherein at a temperature of at least 15° C. the substantially liquid core includes no more than 1.0 weight percent solid 2-chloro-6-(trichloromethyl)pyridine; and
    (b) an aqueous phase, wherein the aqueous phase includes at least about 1.0 weight percent aromatic solvent of a total weight of the microcapsule suspension formulation.

2. The microcapsule suspension formulation according to claim 1, further including:
    at least one ionic stabilizer present in the aqueous phase.

3. The microcapsule suspension formulation according to claim 1, wherein the aromatic solvent present in the aqueous phase is at least one compound selected from the group consisting of: light aromatics, naphthalene depleted light aromatics, heavy aromatics, and naphthalene depleted heavy aromatics.

4. The microcapsule suspension formulation according to claim 3, wherein the aromatic solvent present in the aqueous phase is naphthalene depleted heavy C10-13 aromatics.

5. The microcapsule suspension formulation according to claim 4, wherein the aromatic solvent present in the aqueous phase comprises between about 1% by weight and about 10% by weight naphthalene depleted heavy C10-13 aromatics.

6. The microcapsule suspension formulation according to claim 4, wherein the aromatic solvent present in the aqueous phase, comprises between about 2% by weight and about 5% by weight naphthalene depleted heavy C10-13 aromatics.

7. The microcapsule suspension formulation according to claim 4, wherein the aromatic solvent present in the aqueous phase comprises between about 2.5% by weight and about 3.0% by weight naphthalene depleted heavy C10-13 aromatics.

8. The microcapsule suspension formulation according to claim 3, wherein the aromatic solvent present in the aqueous phase is heavy C10-13 aromatics.

9. The microcapsule suspension formulation according to claim 8, wherein the aromatic solvent present in the aqueous phase comprises between about 1% by weight and about 10% by weight heavy C10-13 aromatics.

10. The microcapsule suspension formulation according to claim 8, wherein the aromatic solvent present in the aqueous phase comprises between about 2% by weight and about 5% by weight heavy C10-13 aromatics.

11. The microcapsule suspension formulation according to claim 8, wherein the aromatic solvent present in the aqueous phase comprises between about 2.5% by weight and about 3.0% by weight heavy C10-13 aromatics.

12. The microcapsule suspension formulation according to claim 1, wherein the microcapsules have a volume median particle size of from about 1 to about 5 microns.

13. The microcapsule suspension formulation according to claim 1, wherein the ratio of the suspended phase a) to the aqueous phase b) is from about 1:0.75 to about 1:100.

14. The microcapsule suspension formulation according to claim 1, wherein the ratio of the suspended phase a) to the aqueous phase b) is from about 1:1 to about 1:7.

15. The microcapsule suspension formulation according to claim 1, wherein the ratio of the suspended phase a) to the aqueous phase b) is from about 1:1 to about 1:4.

16. The microcapsule suspension formulation according to claim 1, wherein the polymeric isocyanate is polymethylene polyphenylisocyanate.

17. A fertilizer composition comprising: a nitrogen fertilizer and the microcapsule suspension formulation according to claim 1.

18. The fertilizer composition according to claim 17, wherein the nitrogen fertilizer is urea ammonium nitrate.

19. A method of suppressing the nitrification of ammonium nitrogen in growth medium comprising the steps of applying the microcapsule suspension formulation of claim 1 to a plant growth medium.

20. The method according to claim 19, wherein the formulation is applied in combination with a pesticide or sequentially with a pesticide.

\* \* \* \* \*